US007932377B2

(12) United States Patent
Sommermeyer

(10) Patent No.: US 7,932,377 B2
(45) Date of Patent: Apr. 26, 2011

(54) COMPLEXING OF MEDICINAL SUBSTANCES WITH HIGH-MOLECULAR CARRIERS AND INJECTION AND INFUSION SOLUTIONS CONTAINING SAID COMPLEXES

(75) Inventor: Klaus Sommermeyer, Rosbach (DE)

(73) Assignee: Supramol Parenteral Colloids GmbH, Rosbach-Rodheim (DE)

( * ) Notice: Subject to any disclaimer, the term of this patent is extended or adjusted under 35 U.S.C. 154(b) by 495 days.

(21) Appl. No.: 10/559,005

(22) PCT Filed: May 28, 2004

(86) PCT No.: PCT/EP2004/005801
§ 371 (c)(1), (2), (4) Date: Feb. 3, 2006

(87) PCT Pub. No.: WO2004/105800
PCT Pub. Date: Dec. 9, 2004

(65) Prior Publication Data
US 2006/0183697 A1    Aug. 17, 2006

(30) Foreign Application Priority Data

May 30, 2003 (DE) .................................. 103 24 710

(51) Int. Cl.
| A61K 31/718 | (2006.01) |
| C08B 31/12 | (2006.01) |
| C08B 31/18 | (2006.01) |
| C08B 33/04 | (2006.01) |
| C08B 33/08 | (2006.01) |
| C08B 35/04 | (2006.01) |
| C08B 35/08 | (2006.01) |

(52) U.S. Cl. ............................ 536/105; 514/60; 536/111
(58) Field of Classification Search .................. None
See application file for complete search history.

(56) References Cited

U.S. PATENT DOCUMENTS

| 2,661,349 A | * | 12/1953 | Caldwell et al. ................. 536/63 |
| 3,455,838 A | * | 7/1969 | Szymanski et al. .......... 428/402.2 |
| 3,892,867 A | * | 7/1975 | Schoonman .................... 426/93 |
| 5,260,050 A | * | 11/1993 | Ranney ........................ 424/9.351 |
| 5,424,419 A | * | 6/1995 | Hasegawa et al. ............. 536/113 |
| 5,612,203 A | * | 3/1997 | Maruo et al. .................... 435/101 |
| 6,132,787 A | * | 10/2000 | Bunger et al. ............. 426/330.3 |

FOREIGN PATENT DOCUMENTS

| EP | 1 106 186 A2 | 6/2001 |
| WO | WO 97/33552 | 9/1997 |
| WO | WO 97/38727 | 10/1997 |
| WO | WO 98/01158 | 1/1998 |
| WO | WO 99/51284 | 10/1999 |
| WO | WO 02/02146 A2 | 1/2002 |
| WO | WO 02/080979 | 10/2002 |
| WO | WO 03/00738 A2 | 1/2003 |
| WO | WO 03/074088 A2 | 9/2003 |

OTHER PUBLICATIONS

2006 Chemical Abstracts Catalog, published by Chemical Abstracts Service, p. 52.*

Kayser, O. et al., "Formulation and Biopharmaceutical Issues in the Development of Drug Delivery Systems for Antiparasitic Drugs," *Parasitol Res*, 90:S63-S70 (2003).

Chowdary, K.P.R., et al., "Biopharmaceutical Studies on Solid Dispersions of Nalidixic Acid in Modified Starches," *Drug Development and Industrial Pharmacy*, 20(19): 3015-3022 (1994).

Chiou, W.L., et al., "Pharmaceutical Applications of Solid Dispersion Systems," *J. Pharm. Sci.*, 60(9): 1281-1302, (Sep. 1971).

Kushida, I., et al., "Improvement of Dissolution and Oral Absorption of ER-34122, A Poorly Water-Soluble Dual 5-Lipoxygenase/Cyclooxygenase Inhibitor with Anti-Inflammatory Activity by Preparing Solid Dispersion," *J. Pharm. Sci.*, 91(1): 258-266, (Jan. 2002).

Jung, J.Y., et al., "Enhanced Solubility and Dissolution Rate of Itraconazole by a Solid Dispersion Technique," *International Journal of Pharmaceutics*, 187:209-218 (1999).

Milby, K.H. et al., "Ion-Exchange Chromatography of Proteins the Effect of Neutral Polymers in the Mobile Phase," Journal of Chromatography, 482:133-144 (1989).

* cited by examiner

*Primary Examiner* — Eric S Olson
(74) *Attorney, Agent, or Firm* — Hamilton, Brook, Smith & Reynolds, P.C.

(57) ABSTRACT

A molecular complex of a high molecular weight carrier substance and of a medicinal substance. The carrier substance has functional groups whereby the carrier substance and the medicinal substance are bound non-covalently. The medicinal substance is insoluble or slightly soluble in water and the carrier substance is readily soluble in water. The carrier substance can be starch or a starch derivative and can have only one functional group for non-covalent binding of the medicinal substance in each molecule.

13 Claims, No Drawings

COMPLEXING OF MEDICINAL SUBSTANCES WITH HIGH-MOLECULAR CARRIERS AND INJECTION AND INFUSION SOLUTIONS CONTAINING SAID COMPLEXES

RELATED APPLICATIONS

This application is the U.S. National Stage of International Application No. PCT/EP2004/005801, filed May 28, 2004, published in German, and claims priority under 35 U.S.C. §119 or 365 to German Application No. 103 24 710.6, filed May 30, 2003.

The present invention relates to complexes of a medicinal substance and a high molecular weight carrier, and to injection and infusion solutions which comprise these complexes. The invention further relates to processes for producing such injection and infusion solutions by the high molecular weight carriers being functionalized, reacted with the medicinal substance and dissolved in an aqueous solution.

Covalent chemical bonding of pharmaceutical medicinal substances to high molecular weight carriers such as, for example, polysaccharides, proteins or polyethylene glycols is a known process for increasing for example the water solubility of compounds which are intrinsically insoluble in water or slightly soluble. Such conjugates may also advantageously have considerably prolonged plasma half-lives as a result of the increase in the molecular weight of the active pharmaceutical ingredient compared with the underivatized medicinal substance. It is also possible by this technique to reduce the antigenicity of therapeutic proteins and thus reduce the immunogenic side effects thereof (compare Abuchowski and Davis, Enzymes as drugs, Holcenberg and Rubberts, editors, pp 367-383, John Wiley & Sons N.Y. (1981)).

Examples of such conjugates and their advantages compared with the isolated medicinal substances are described inter alia in WO 98/01158, WO 03/000738 A2, WO 02/080979, WO 97/33552 and WO 97/38727.

Although such covalent coupling products based on polysaccharides or else based on polyethylene glycol derivatives are now in wide use, a substantial disadvantage of this technology must be pointed out.

Covalent linkage of a medicinal substance to a macromolecule such as, for example, hydro-ethyl starch or polyethylene glycol results in a new chemical compound which is likewise a medicinal substance. This compound must, for reasons derived from pharmaceutical legislation, be subjected anew to relatively elaborate, costly and time-consuming testing of its safety and efficacy in relation to its safety and efficacy, even if the medicinal substance per se is well characterized in this regard.

It is therefore an object of the invention to provide medicinal substances which have the abovementioned advantages of covalent coupling products consisting of medicinal substances and polymeric carrier substances but which do not need to be subjected to such an elaborate testing.

It is a further object of the invention to provide medicinal substances which have the above-mentioned advantages of covalent coupling products consisting of medicinal substances and polymeric carrier substances but which can be produced more cost-effectively.

It is likewise an object of the invention to provide infusion solutions and injection solutions having medicinal substances which have the abovementioned advantages of covalent coupling products of medicinal substances and polymeric carrier substances but which do not need to be subjected such an elaborate testing.

A further object of the invention is to provide a process with the aid of which compounds which achieve the objects indicated above are prepared.

It is surprisingly possible to achieve the abovementioned objects according to invention by molecular complexes of a high molecular weight carrier substance and of a medicinal substance, where the carrier substance has functional groups whereby the medicinal substances are bound non-covalently in a complex.

Such non-covalent bindings are, for example, associative bindings such as hydrogen bonds, salt bindings or mechanical aggregates brought about, for example, by interlockings at the molecular level. Complexes are according to the invention when the dissolving behavior of the medicinal substance in a solvent in which the high molecular weight carrier substance is soluble is adapted to the dissolving behavior of the high molecular weight carrier substance without the two molecules being covalently bonded together. Specifically, this means that the solubility of an insoluble or slightly soluble medicinal substance is improved when the high molecular weight carrier substance is readily soluble in this medium. This medium is preferably an aqueous solution.

The solubility of a medicinal substance which is insoluble or slightly soluble in water at room temperature is preferably improved by the addition of a high molecular weight carrier substance by a factor of at least 100, particularly preferably by a factor of at least 1000, in particular by a factor of at least 10 000.

There is no limitation on the ratio by weight of medicinal substance and high molecular weight carrier substance. However, the ratio preferably chosen is one at which a pharmacologically effective amount of medicinal substance is dissolved in a solution of the complex, and the concentration of the high molecular weight carrier substance in such a solution is preferably greater than 5% by weight, particularly preferably greater than 10% by weight and especially greater than 20% by weight.

Both the high molecular weight carrier substance and the medicinal substance are preferably pharmacologically acceptable and are marketed as ingredients of medicinal products. In contrast to the covalently bonded substances which must undergo costly and time-consuming testing, the complexes according to the invention comprise only a physical mixture of components which are acceptable per se, so that the final product now needs to be subjected only to a reduced clinical safety testing.

A high molecular weight carrier substance means in the context of the invention any molecule which can be administered to a patient and has a weight average molecular weight above 500 Daltons. The molecular weight of the high molecular weight component is preferably in the range from 1000 to 1 000 000 Daltons, particularly preferably in the range from 3000 to 300 000 Daltons and especially from 6000 to 16 000 Daltons.

Examples of high molecular weight carrier substances are polyethylene glycols, polypeptides and proteins, and polysaccharides. Particularly preferred polysaccharides are starch and starch derivatives, including degradation products thereof.

High molecular weight carrier substances are preferably soluble in water. Water-soluble starch derivatives are very particularly preferred, especially hydroxyethyl starch. Here again, HES is preferred.

HES is the hydroxyethylated derivative of the glucose polymer amylopectin which constitutes more than 95% of waxy corn starch. Amylopectin consists of glucose units which are present in α-1,4-glycosidic linkages and have α-1, 6-glycosidic branches. HES has advantageous rheological properties and is currently employed clinically as volume replacement agent and for hemodilution therapy (Sommermeyer et al., Krankenhauspharmazie, Vol. 8 (8, 1987) pages 271-278 and Weidler et al., Arzneimittelforschung 1 Drug Res., 41, (1991) pages 494-498).

HES is characterized essentially by the weight average molecular weight $M_w$, the number average molecular weight $M_n$, the molecular weight distribution and the substitution level. Substitution with hydroxyethyl groups in ether linkage is in this case possible at carbon atoms 2 (C2), 3 (C3) and 6 (C6) of the anhydroglucose units. The substitution pattern is in this case described as the ratio of the substitution at C2 and C6 (C2/C6 ratio). The substitution level can in this connection be described as DS ("degree of substitution"), which is based on the substituted glucose molecules as a proportion of all the glucose units, or as MS ("molar substitution"), which refers to the average number of hydroxyethyl groups per glucose unit.

In the scientific literature, the molecular weight $M_w$ in the unit of kDaltons together with the substitution level MS is stated as brief description of hydroxyethyl starch. Thus, HES 10/0.4 is the designation for a hydroxyethyl starch with a weight average molecular weight $M_w$ of 10 000 Daltons and a substitution level MS of 0.4.

There is no limitation on the molecular substitution level. The molecular substitution level MS is preferably in the range from 0.05 to 1.5, particularly preferably in the range from 0.1 to 0.8 and especially in the range from 0.3 to 0.5.

There is no limitation on the C2/C6 ratio. This ratio is preferably greater than 1, and this ratio is particularly preferably greater than 2 and especially greater than 9.

A particularly preferred complex according to the invention is one in which only respectively one molecule of a high molecular weight carrier substance is bound to respectively only one medicinal substance by non-covalent binding. It is particularly preferred for the high molecular weight carrier substance to have only one functional group for non-covalent binding of the medicinal substance in each molecule.

The functional group is preferably an acidic or a basic group.

If the high molecular weight carrier substance is a polysaccharide, it is preferred for the high molecular weight carrier substance to have the functional group at the previously reducing end.

It is particularly preferred in this connection for the functional group to be in the case of an acidic functional group an aldonic acid group.

In the case of a basic functional group, a primary amino group is preferred. It is particularly preferred in the case of polysaccharides for the primary amino group to be covalently bonded to an aldonic acid group by conjugation of an aliphatic diamine via an amide bond. It is particularly preferred for this aldonic acid group to be present at the previously reducing end of the polysaccharide chain.

The formation of an aldonic acid group at the reducing end of a polysaccharide is known. This can take place for example by selective oxidation using a mild oxidizing agent such as, for example, hypoiodide.

The formation of a primary amino group by conjugation of an aliphatic diamine which is covalently bonded to an aldonic acid group by an amide bond is likewise known. This can take place for example by reacting the diamine with the polysaccharide aldonic acid.

One example of the formation of an aldonic acid group at the reducing end of a polysaccharide is the preparation of hydroxyethylstarch-aldonic acid starting from hydroxyethyl starch. Hydroxyethyl starch can be oxidized, for example as disclosed in WO 02/080979, selectively at the reducing end group with hypoiodide to give the carboxylic acid, resulting in hydroxyethylstarch-aldonic acid.

One example of the formation of an amino group at the reducing end of a polysaccharide is the preparation of amino-functionalized hydroxyethyl starch starting from hydroxyethylstarch-aldonic acid. This is described in WO 02/080979 for the reaction of hydroxyethylstarch-aldonic acid with an aliphatic diamine.

It is possible to use all medicinal substances to form a complex according to the invention. Preferred medicinal substances are those already authorized under pharmaceutical legislation. Preference is likewise given to medicinal substances which already have a functional group making complex binding possible. Examples of such groups may be basic or acidic groups. Preference is equally given to medicinal substances whose solubility in water is poor or zero.

A particular embodiment of the invention is represented by complexes of HES-aldonic acid as high molecular weight component and of a medicinal substance selected from the group consisting of the polyene macrolide antibiotics amphotericin B, nystatin and natamycin.

In this embodiment, HES-aldonic acid preferably has a weight average molecular weight of from 1000 to 300 000 Daltons, a molar substitution level of from 0.1 to 0.5 and a C2/C6 ratio of from 2 to 11.

In this embodiment, HES-aldonic acid particularly preferably has a weight average molecular weight of from 6000 to 16 000 Daltons, a molar substitution level of from 0.35 to 0.45 and a C2/C6 ratio of from 9 to 11.

In this embodiment in particular, complexes of such a particularly preferred HES-aldonic acid with the polyene macrolide antibiotic amphotericin B are preferred.

Complexes of HES-aldonic acid as high molecular weight component and the medicinal substance antiarrhythmic amiodarone represent a particular embodiment of the invention. In this embodiment, HES-aldonic acid preferably has a weight average molecular weight of from 1000 to 300 000 Daltons, a molar substitution level of from 0.1 to 0.5 and a C2/C6 ratio of from 2 to 11.

In this embodiment, HES-aldonic acid particularly preferably has a weight average molecular weight of from 6000 to 16 000 Daltons, a molar substitution level of from 0.35 to 0.45 and a C2/C6 ratio of from 9 to 11.

Complexes of HES-aldonic acid as high molecular weight component and the medicinal substance vancomycin represent a further particular embodiment of the invention. In this embodiment, HES-aldonic acid preferably has a weight average molecular weight of from 1000 to 300 000 Daltons, a molar substitution level of from 0.1 to 0.5 and a C2/C6 ratio of from 2 to 11.

In this embodiment, HES-aldonic acid particularly preferably has a weight average molecular weight of from 6000 to 16 000 Daltons, a molar substitution level of from 0.35 to 0.45 and a C2/C6 ratio of from 9 to 11.

It is preferred for a complex according to the invention to be soluble in water.

It is likewise preferred for it to be possible to administer the complex according to the invention parenterally to a patient.

Injection solutions and infusion solutions can be obtained by dissolving complexes according to the invention in a suitable carrier solution. Injection solutions and infusion solutions can be obtained by using carrier solutions for preparing solutions according to the invention. These carrier infusion solutions are preferably aqueous solutions. In a particular embodiment, the aqueous carrier solutions are isotonic solutions, for example isotonic glucose solutions.

The complexes according to the invention can be prepared by dissolving the high molecular weight carrier substance and the medicinal substance in an aqueous solution, where appropriate with heating. The aqueous solution is preferably an isotonic solution. In order to prevent oxidation of the components, operation under a protective atmosphere is preferred. The resulting solution is then preferably filtered, particularly preferably filtered for sterilization.

The concentration of the medicinal substance in such a solution is preferably in the pharmacologically effective range. There is no limitation on the concentration of the high molecular weight carrier. However, this concentration is preferably greater than 5% by weight, particularly preferably greater than 10% by weight and especially greater than 20% by weight, based on the finished solution.

Complexes according to the invention, preferably in the case of medicinal substances which are insoluble in water, can also be prepared by dissolving the high molecular weight component and the medicinal substance in a common solvent in which both components are soluble. Such solvents may be, for example, polar, aprotic solvents such as dimethyl sulfoxide (DMSO), dimethylacetamide (DMA) or dimethylformamide (DMF). Moreover, oxidation of the components is avoided by operating where appropriate under protective gas. After sterilization by filtration, the solvent is removed under mild conditions, for example by freeze-drying.

The solvent-free substance obtained in this way can be used for example as starting material for producing an injection product or infusion product.

To this end, the solvent-free substance obtained in this way can be dissolved in an aqueous solution, for example in a small volume of water for injections, and then in a compatible carrier infusion solution such as, for example, 5% by weight glucose solution. The concentration of the soluble complex must in this case be chosen so that the solution shows neither turbidity nor particle formation nor other changes even after prolonged storage, and thus exhibits the characteristics of injectable pharmaceutical forms. In this case too, operation under protective gas is preferred.

The concentration of the medicinal substance in such a solution is preferably in the pharmacologically effective range. There is no limitation on the concentration of the high molecular weight carrier. However, this concentration is preferably greater than 5% by weight, particularly preferably greater than 10% by weight and especially greater than 20% by weight, based on the finished solution.

This process is particularly preferred for producing injection solutions and infusion solutions according to the invention which have a complex of HES-aldonic acid and of a polyene macrolide antibiotic.

The solutions, produced in this way, of the complexes according to the invention represent starting materials for finished medicinal products which have long-term storage stability and are in the form of injection solutions or infusion solutions which can be administered to the patient without further manipulation.

The invention is explained within the scope of specific embodiments in the following examples. However, no limitation is intended thereby.

EXAMPLES

Example 1

Preparation of Amphotericin B Complexes with HES 1010.4 Aldonic Acid 1 g of HES 10/0.4 aldonic acid, which was prepared by a literature method and had a C2/C6 ratio of >10, was dissolved in 10 ml of dimethyl sulfoxide (DMSO). 50 mg of amphotericin B complying with Ph. Eur. are added to the solution and, after dissolving is complete, the mixture is filtered to remove particles and sterilized through a 0.45 μm filter.

The solution is then freeze-dried.

The lyophilizate dissolves smoothly in 10 ml of water to give a clear, transparent solution with a yellow-orange color. This solution is diluted further to a total volume of 100 ml with 5% by weight glucose solution for infusion. The resulting solution remains clear, transparent and particle-free even after storage in a refrigerator for several months.

Comparative Example 1

Attempt to Prepare an Amphotericin B—HES 10/0.4 Complex

The attempt is carried out as described in Example 1 with the difference that HES 10/0.4 was used instead of HES 10/0.4 aldonic acid. However, the product after lyophilization no longer dissolves in 10 ml of water; on the contrary, a turbid, yellow-orange suspension of amphotericin B remains.

Comparative Example 2

Attempt to Prepare a Gluconic Acid—Amphotericin B Complex

The attempt is carried out as described in Example 1 with the difference that 1 g of glucose was used instead of HES 10/0.4 aldonic acid, and the amount of gluconic acid (18 mg-0.1 mmol) equimolar to the amount of HES 10/0.4 aldonic acid employed in Example 1 was used.

It is not possible after lyophilization to dissolve the solution in 10 ml of water; on the contrary, a suspension of amphotericin B remains.

Example 2

Production of an Amiodarone Injection Solution 10 g of HES-aldonic acid 10/0.4 are dissolved in 30 ml of water for injections at about 50° C. 3 g of amiodarone hydrochloride are added to the solution, and the temperature is maintained until a clear solution results. It is then diluted with the same volume of a 10% by weight glucose solution in water for injections, and the solution is cooled to room temperature. The pH is then adjusted to 3.4 with sodium hydroxide solution. After sterilization by filtration, the solution is dispensed aseptically into ampoules. The resulting solution remains clear, transparent and particle-free even after storage in a refrigerator for several months.

Example 3

Production of a Vancomycin Injection Solution 510 mg of vancomycin HCl 500 mg of vancomycin base are dissolved in 8 ml of a 25% by weight solution of HES 10/0.4 aldonic acid in distilled water. The pH of the solution is adjusted to pH 7.3 with 0.1N sodium hydroxide solution (about 4 ml). The solution remains clear during this.

It is then sterilized by filtration with a 0.2 μm membrane filter and dispensed into vials. The resulting solution remains clear, transparent and particle-free even after storage in a refrigerator for several months.

Comparative Example 3

The attempt is carried out in analogy to Example 3, with the difference that HES 10/0.4 is used instead of HES 10/0.4 aldonic acid. The resulting solution becomes turbid after 2-3 hours, and vancomycin precipitates.

Comparative Example 4

The attempt is carried out in analogy to Example 3, with the difference that distilled water is used instead of HES 10/0.4 aldonic acid. The resulting solution becomes turbid after a few minutes, and vancomycin precipitates.

Example 4

Production of a Vancomycin Injection Solution 500 mg of vancomycin base (prepared from vancomycin chloride by addition of an equimolar amount of sodium hydroxide solution to precipitate from concentrated aqueous solution) are mixed with 10 ml of a 20% by weight HES 10/0.4 aldonic acid solution in distilled water.

The base dissolves (pH 7.0). After sterilization by filtration with a 0.2 µm membrane filter, the solution is dispensed into vials.

The resulting solution remains clear, transparent and particle-free even after storage in a refrigerator for several weeks.

The invention claimed is:

1. A molecular complex of a high molecular weight carrier substance and of a medicinal substance, where the carrier substance has functional groups whereby the carrier substance and the medicinal substance are bound non-covalently, wherein
the medicinal substance is insoluble or slightly soluble in water,
the carrier substance is readily soluble in water,
the carrier substance is an optionally substituted starch and has only one functional group at the previously reducing end for non-covalent binding of the medicinal substance in each molecule, wherein the functional group is a primary amino group,
the complex is water soluble,
the carrier substance has a weight average molecular weight of from 1000 to 1 000 000 Daltons,
the medical substance comprises a functional group making complex binding possible selected from the group consisting of a basic group and an acidic group, the complex is solvent-free.

2. The complex as claimed in claim 1, wherein the complex can be administered parenterally.

3. The complex as claimed in claim 1, wherein the primary amino group is bound to an aldonic acid group by conjugation of an aliphatic diamine by means of an amide bond.

4. A molecular complex of a high molecular weight carrier substance and of a medicinal substance, where the carrier substance has functional groups whereby the carrier substance and the medicinal substance are bound non-covalently, wherein
the medicinal substance is insoluble or slightly soluble in water,
the carrier substance is readily soluble in water,
the carrier substance is hydroxyethyl starch (HES) and has only one functional group for non-covalent binding of the medicinal substance in each molecule, wherein the functional group is an acidic or a basic group,
the complex is water soluble,
the carrier substance has a weight average molecular weight of from 1000 to 1 000 000 Daltons,
the medical substance comprises a functional group making complex binding possible selected from the group consisting of a basic group and an acidic group, the complex is solvent-free.

5. A molecular complex of a high molecular weight carrier substance and of a medicinal substance, where the carrier substance has functional groups whereby the carrier substance and the medicinal substance are bound non-covalently, wherein
the medicinal substance is insoluble or slightly soluble in water,
the carrier substance is readily soluble in water,
the carrier substance is an optionally substituted starch and has only one functional group for non-covalent binding of the medicinal substance in each molecule, wherein the functional group is an acidic or a basic group,
the complex is water soluble,
the carrier substance has a weight average molecular weight of from 1000 to 1 000 000 Daltons,
the medical substance comprises a functional group making complex binding possible selected from the group consisting of a basic group and an acidic group, the complex is solvent-free, wherein the optionally substituted starch is hydroxyethyl starch (HES), and wherein the medicinal substance is selected from the group consisting of the polyene macrolide antibiotics amphotericin B, nystatin and natamycin.

6. The complex as claimed in claim 5, wherein the optionally substituted starch is a HES-aldonic acid, and wherein the HES-aldonic acid has a weight average molecular weight of from 1000 to 300 000 Daltons, a molar substitution level of from 0.1 to 0.5 and a C2/C6 ratio of from 2 to 11.

7. The complex as claimed in claim 6, wherein the HES-aldonic acid has a weight average molecular weight of from 6000 to 16 000 Daltons, a molar substitution level of from 0.35 to 0.45 and a C2/C6 ratio of from 9 to 11, and the medicinal substance is amphotericin B.

8. The complex as claimed in claim 4, wherein the functional group of hydroxyethyl starch is an aldonic acid, forming a HES-aldonic acid, and wherein the HES-aldonic acid has a weight average molecular weight of from 6000 to 16 000 Daltons, a molar substitution level of from 0.35 to 0.45 and a C2/C6 ratio of from 9 to 11, and the medicinal substance is the antiarrhythmic amiodarone.

9. An injection solution comprising, a complex as claimed in claim 1.

10. An infusion solution comprising, a complex as claimed in claim 1.

11. A process for preparing complexes as claimed in claim 1, wherein the medicinal substance and the high molecular weight carrier substance are dissolved in a compatible solvent, and the solvent is removed from the resulting solution by freeze-drying.

12. A process for producing an injection solution or an infusion solution, wherein a complex as claimed in claim 1 is dissolved in an aqueous solution.

13. A molecular complex of a high molecular weight carrier substance and of a medicinal substance, where the carrier substance has functional groups whereby the carrier substance and the medicinal substance are bound non-covalently, wherein
the medicinal substance is insoluble or slightly soluble in water,
the carrier substance is readily soluble in water, the carrier substance is an optionally substituted starch and has only one functional group for non-covalent binding of the medicinal substance in each molecule, wherein the functional group is an acidic or a basic group, the complex is water soluble, the carrier substance has a weight average molecular weight of from 1000 to 1 000 000 Daltons, the medical substance comprises a functional group making complex binding possible selected from the group consisting of a basic group and an acidic group, the complex is solvent-free, wherein the medicinal substance is a macrolide.

* * * * *